(12) United States Patent
Horváth et al.

(10) Patent No.: US 10,529,498 B2
(45) Date of Patent: Jan. 7, 2020

(54) NANOWIRES OF ORGANIC-INORGANIC PEROVSKITES

(71) Applicant: ECOLE POLYTECHNIQUE FEDERALE DE LAUSANNE (EPFL), Lausanne (CH)

(72) Inventors: Endre Horváth, Lausanne (CH); László Forró, Ecublens (CH); Massimo Spina, Renens (CH)

(73) Assignee: ECOLE POLYTECHNIQUE FÉDÉRALE DE LUASANNE (EPFL), Luasanne (CH)

( * ) Notice: Subject to any disclaimer, the term of this patent is extended or adjusted under 35 U.S.C. 154(b) by 0 days.

(21) Appl. No.: 15/313,153

(22) PCT Filed: May 22, 2015

(86) PCT No.: PCT/IB2015/053792
§ 371 (c)(1),
(2) Date: Nov. 22, 2016

(87) PCT Pub. No.: WO2015/177770
PCT Pub. Date: Nov. 26, 2015

(65) Prior Publication Data
US 2017/0098513 A1    Apr. 6, 2017

Related U.S. Application Data

(63) Continuation of application No. PCT/IB2014/061649, filed on May 23, 2014.

(51) Int. Cl.
*H01G 9/20* (2006.01)
*C01G 19/00* (2006.01)
(Continued)

(52) U.S. Cl.
CPC ......... *H01G 9/2004* (2013.01); *C01G 17/006* (2013.01); *C01G 19/006* (2013.01);
(Continued)

(58) Field of Classification Search
None
See application file for complete search history.

(56) References Cited

U.S. PATENT DOCUMENTS 5,825,033 A * 10/1998 Barrett .............. H01L 27/14658
250/370.09
6,498,358 B1 * 12/2002 Lach ...................... G02F 1/025
257/183
2015/0287852 A1 * 10/2015 Leung ................ H01L 51/4226
136/263

OTHER PUBLICATIONS

Spina et al., Controlled growth of CH3NH3PbI3 nanowires in arrays of open nanofluidic channels, Scientific Reports, 6:19834, DOI: 10.1038/srep19834, Jan. 25, 2015, pp. 1-7.
(Continued)

*Primary Examiner* — Clinton A Brooks
(74) *Attorney, Agent, or Firm* — The Law Office of Joseph L. Felber

(57) ABSTRACT

An organic-inorganic perovskite $CH_3NH_3PbI_3$ nanowire showing a length-width aspect ratio from 5-400 up to $10^9$ and a width-height ratio of 1-100 up to 1-10000. Further, the invention is embodied as a process for making the nanowire wherein at least a polar aprotic solvents is used, the polar aprotic solvent being at least one from the list comprising DMF, DMSO, and DMAc solvents.

8 Claims, 14 Drawing Sheets

(51) Int. Cl.
  C01G 17/00    (2006.01)
  C07F 7/00     (2006.01)
  C07C 211/63   (2006.01)
  H01L 51/00    (2006.01)
  H01L 51/42    (2006.01)
  H01L 51/50    (2006.01)
(52) U.S. Cl.
  CPC ............ *C07C 211/63* (2013.01); *C07F 7/003* (2013.01); *H01L 51/0077* (2013.01); *C01P 2002/34* (2013.01); *C01P 2004/16* (2013.01); *C01P 2004/54* (2013.01); *H01G 9/20* (2013.01); *H01L 51/42* (2013.01); *H01L 51/5012* (2013.01); *Y02E 10/549* (2013.01); *Y02P 70/521* (2015.11)

(56) References Cited

OTHER PUBLICATIONS

Endre Horvath et al: "Nanowires of Methylamonium Lead Iodide (CH 3 NH 3 PbI 3 ) Prepared by Low Temperature Solution-Mediated Crystallization", Nano Letters, vol. 14, No. 12, Oct. 29, 2014 (Oct. 29, 2014), pp. 6761-6766.

Jeong-Hyeok Im et al: "Nanowire Perovskite Solar Cell", Nano Letters, vol. 15, No. 3, Feb. 24, 2015 (Feb. 24, 2015), pp. 2120-2126.

Hui-Seon Kim et al: "High Efficiency Solid-State Sensitized Solar Cell-Based on Submicrometer Rutile TiO 2 Nanorod and CH 3 NH 3 PbI 3 Perovskite Sensitizer", Nano Letters, vol. 13, No. 6, May 14, 2013 (May 14, 2013), pp. 2412-2417.

Dae-Yong Son et al: "11% Efficient Perovskite Solar Cell Based on ZnO Nanorods: An Effective Charge Collection System", Journal of Physical Chemistry C, vol. 118, No. 30, Mar. 7, 2014 (Mar. 7, 2014), pp. 16567-16573.

International Search Report for application PCT/IB2015/053792, dated Dec. 17, 2015.

Written Opinion for application PCT/IB2015/053792, dated Dec. 17, 2015.

Office Action for the European Patent Office for Application 15 734 724.6-1106, dated Feb. 26, 2-18.

\* cited by examiner

| Reference | Material | Configuration | R (A/W) | EQE (%) | Response time (s) | Light source (nm) | $V_{SD}$ (V) | $V_G$ (V) |
|---|---|---|---|---|---|---|---|---|
| This Work | CH$_3$NH$_3$PbI$_3$ | Nanowires | 0.005 | 0.4 | <0.0005 | 633 | 1 | 0 |
| Liu et al. Nature Nano 2014[3] | Graphene, single layer (SLG) | Stacked SLG-Ta$_2$O$_5$-SLG | 10$^7$ | ~233x10$^6$ | <0.5 | 532 | 1 | 0 |
| Zhang et al. Nature Sci. Rep. 2014[4] | Graphene/ MoS$_2$ | Stacked SLG/SL-MoS$_2$ | 1.2x10$^7$ | 265x 10$^7$ | - | 650 | 1 | -10 |
| Jin et al. J. of Mat. Chem. 2014[5] | Graphene/ HfO$_2$/ CdSe | Stacked SLG - HfO$_2$ - CdSe nanowire | 1.06x10$^7$ | 208x10$^7$ | 0.3-20 | 633 | 1 | -1.5 |
| Britnell et al. Science 2013[6] | TMDCs/ Graphene | Stacked SLG-WS$_2$-SLG | 0.1 | 30 | - | 633 | 0 | ±20 |
| Lopez-Sanchez et al. Nature Nano 2013[7] | MoS$_2$ | SL-MoS$_2$ | 880 | ~195x10$^6$ | 4-9 | 561 | 8 | -70 |
| Zhang et al. Nature Comm. | Graphene | SLG Quantum dot-like array | 0.0086 | 0.02 | - | 532 | 0.1 | - |

Figure 15

NANOWIRES OF ORGANIC-INORGANIC PEROVSKITES

FIELD OF INVENTION

The invention relates to elongated organic-inorganic perovskites, in particular hyper-branched or aligned nano- and microwires parallel or perpendicular to a substrate.

PRIOR ART

Perovskites, the structural analogues of the natural crystal of calcium titanium oxide cover a broad range of versatile materials, which have potential applications in multiple fields such as superconductors, sensorics, fuel cells, ferroelectrics and thermoelectrics. The recently rediscovered, half century old members of this family[1], the organolead halide perovskites turned out to be promising components of next generation solar cells[2]. Incorporated as a sensitizer in mesoscopic solar cells a remarkable power conversion efficiency of 16.2% was demonstrated in lab scale devices[3]. It has been shown that aside from the role of the light absorber the organolead halide perovskites can be viewed both as electron and hole transporting media due to their ambipolar charge transport character[4]. So far, the highest solar-to electric conversions have been reached based on two main compounds (the $CH_3NH_3PbI_3$ and $CH_3NH_3PbI_{3-x}Cl_x$, abbreviated as $MAPbI_3$ and $MAPbI_{3-x}Cl_x$) showing minor alterations in halide content[5,6]. These are direct band gap semiconductors with high absorption coefficient, a favorable band gap of 1.5-1.65 eV and electron-hole diffusion length ranging from ≈100 nm to ≈1 micron[7,8,9]. However, the structural and electronic differences between the two materials, as well as the exact role of the Cl anions have yet to be undoubtedly revealed by the scientific community. Colella et. al.[10] observed that incorporation of Cl as a dopant dramatically improves the charge transport within the perovskite layer. Others observed that the Cl inclusion enhances the granular morphology resulting in a more homogenous current production probed by electron beam-induced current (EBIC) method[11]. Very recently, by inserting formamidinium cations into a lead iodide structure, nearly cubic phase (band gap≈1.43 eV) perovskite was reported, with an absorption edge broadened by 30 nm as compared to $MAPbI_3$[12]. These findings validate the bandgap engineering strategies, where the bandgap of the material might be efficiently tuned by choosing the halide anion and the organic amide constituent[13,14,15]. One of the key aspects towards a low-cost technology capable of competing with the established silicon technology lies in the material s low temperature solution processability. The current approach is based on a single step deposition of a mixture of $PbX_2$ and $CH_3NH_3X$ (X is a halide anion) in a common solvent or sequential deposition of the constituents from a solution onto a mesopourous scaffold[16,17]. Rapid crystallization of the perovskite has been observed during the spin-coating process. In order to obtain an optimized device performance, very often a post-annealing treatment is required. Recent results[18] demonstrated an efficiency of 15% on devices entirely processed below 150° C. The general observation is that minor alteration of the applied processing parameters may lead to dramatically different device performances. This indicates that it is critical to have fine control over the nucleation and crystal growth of the $MAPbI_3$. In their effort to control the morphology of the trihalide perovskite films, Eperon et al.[19] showed that the highest photocurrents were attainable only with the highest perovskite surface coverage.

This prior work suggests that the final crystalline morphology depends mainly on the dynamics of annealing, which will ultimately govern the solvent evaporation, pore voiding or closing and the film thickness. Liu and co-workers reported[20] that the solution-cast films onto a compact $TiO_2$-layer over an FTO-coated glass inhomogeneously covered the substrate and that it was composed of crystalline 'platelets' with the length on the scale of tens of micrometres. The crystallite sizes determined from X-ray diffraction were larger than 400 nm. On the other hand, studies based on electron microscopy observations report the presence of small, ~6 nm nanoparticles supported by surface-modified mesoporous $TiO_2$ film prepared by solution processing.[21] As it is well known, the dimensionality and morphology of crystallites may have a striking influence on their chemical and physical properties. Under most circumstances, nano- and micron sized particles with isotropic particle shapes have been observed. This suggests that the crystallites tend to grow uniformly along the three major crystallographic directions. This can be easily accepted, since $MAPbI_3$ more likely crystallizes in a cubic structure, therefore, in principle there should be no crystallographic driving force for anisotropic growth. Surprisingly, we found that some solvents induce highly anisotropic crystallization of $MAPbI_3$. According to the authors' knowledge, to date, no 1D form of organolead halide perovskites has been observed.

Here we report the synthesis of two sets of $MAPbI_3$ nanowires with mean diameter of 50 and 400 nm and length up to 10 μm. They were prepared through a simple slip-coating approach. The one dimensional form of $MAPbI_3$ could have unique optical and electrical properties. The feasibility of anisotropic growth of organolead halide perovskites opens up a new strategy towards the realization of low-temperature, solution processed films with controlled morphology.

SUMMARY OF INVENTION

In one aspect the invention provides an organic-inorganic perovskite nanowire showing a length-width aspect ratio from 5-400 up to $10^9$ and a width-height ratio of 1-100 up to 1-10000.

In a preferred embodiment, the nanowire is composed of lead methylamine iodide ($CH_3NH_3PbI_3$).

In a further preferred embodiment, the nanowire is composed of $ABX_3$ where A is an aliphatic amine and/or alkali cation, B is a transition metal, noble metal, such as Ge, or Sn cation, and X is a Cl, Br or I anion.

In a further aspect, the invention provides a process for making a nanowire as previously described, wherein at least a polar aprotic solvents is used, the polar aprotic solvent being at least one from the list comprising DMF, DMSO, and DMAc solvents.

In a further preferred embodiment, the process further comprises at least one of steps of solution mixing, slip-coating, spin coating, dip coating, screen printing, doctor blading or spraying.

In a further preferred embodiment, the process further comprises setting a temperature to a value between 273 K and 373 K.

In a further preferred embodiment, the process further comprises using voids on a surface, or pores as a growth directing tool.

In a further aspect, the invention provides a mesoscopic or planar heterojunction single or tandem solar cell made of nanowires as defined herein above in the present section.

In a further aspect, the invention provides a gamma-ray, or X-ray, or visible light, or near infrared detector made of nanowires as defined herein above in the present section.

In a further aspect, the invention provides a light amplification by stimulated emission of radiation system made of nanowires as defined herein above in the present section.

In a further aspect, the invention provides a LED or OLED made of nanowires as defined herein above in the present section.

In a further aspect, the invention provides a magneto-optical data storage element made of nanowires as defined herein above in the present section.

BRIEF DESCRIPTION OF THE FIGURES

The invention will be better understood in light of the description of preferred and example embodiments and in reference to the figures, wherein

FIG. 15 is a table containing a compilation of several recent photodetectors made of nanomaterials.

DESCRIPTION OF PREFERRED AND EXAMPLE EMBODIMENTS OF THE INVENTION

Figure 1:
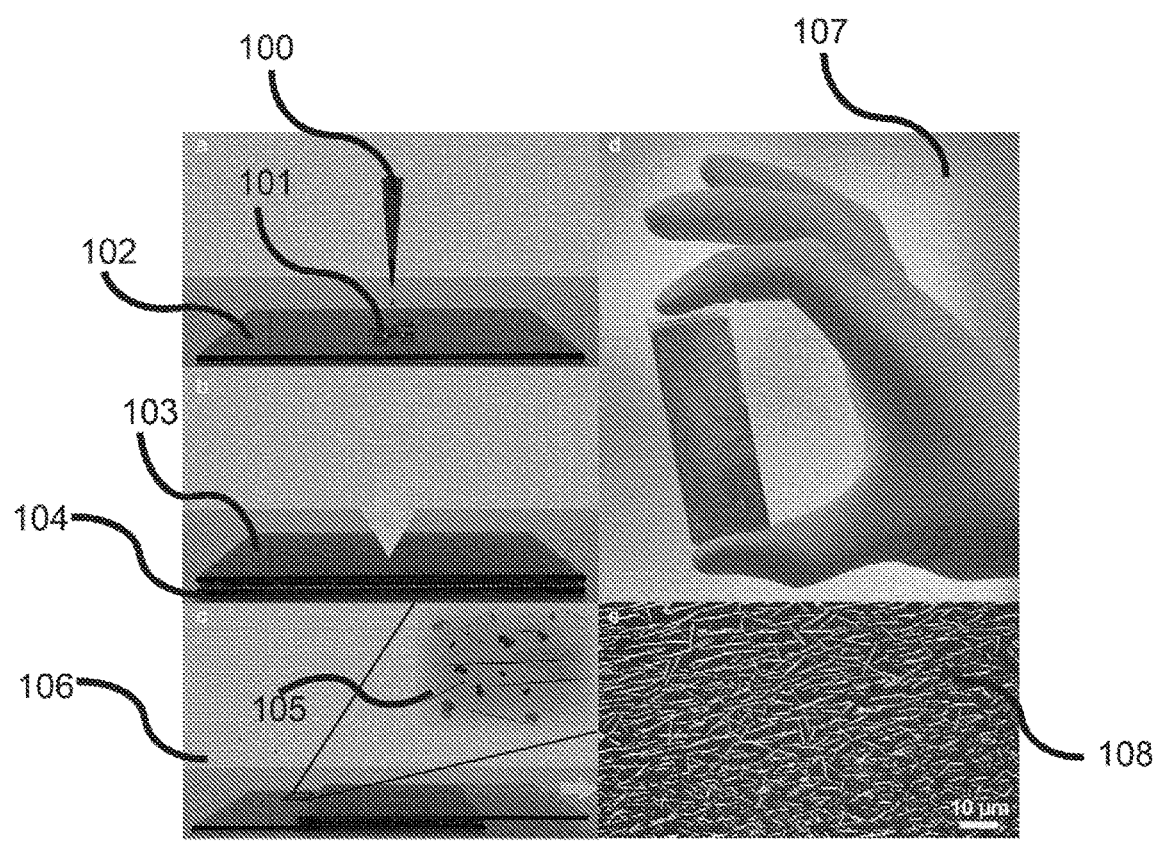
FIG. 1 illustrates steps for obtaining nanowires on a glass slide.

Referring to FIG. 1, saturated solution of $MAPbI_3$ in dimethyl formamide (DMF) (100) was dropped (101) onto a glass microscope slide (102) and covered with a second glass slide so that the excess yellow solution squeezed out; the rest forming a homogenous liquid film between the glass plates (103,104). The excess of the $MAPbI_3$ solution was removed from the sides by soaking with a tissue. Next, the bottom substrate was held in place while gradually sliding the upper glass plate, exposing the thin liquid film to air (106). Solvent evaporation from the uncovered surface caused an instantaneous yellow to brown-red color change (107).

Figure 2:
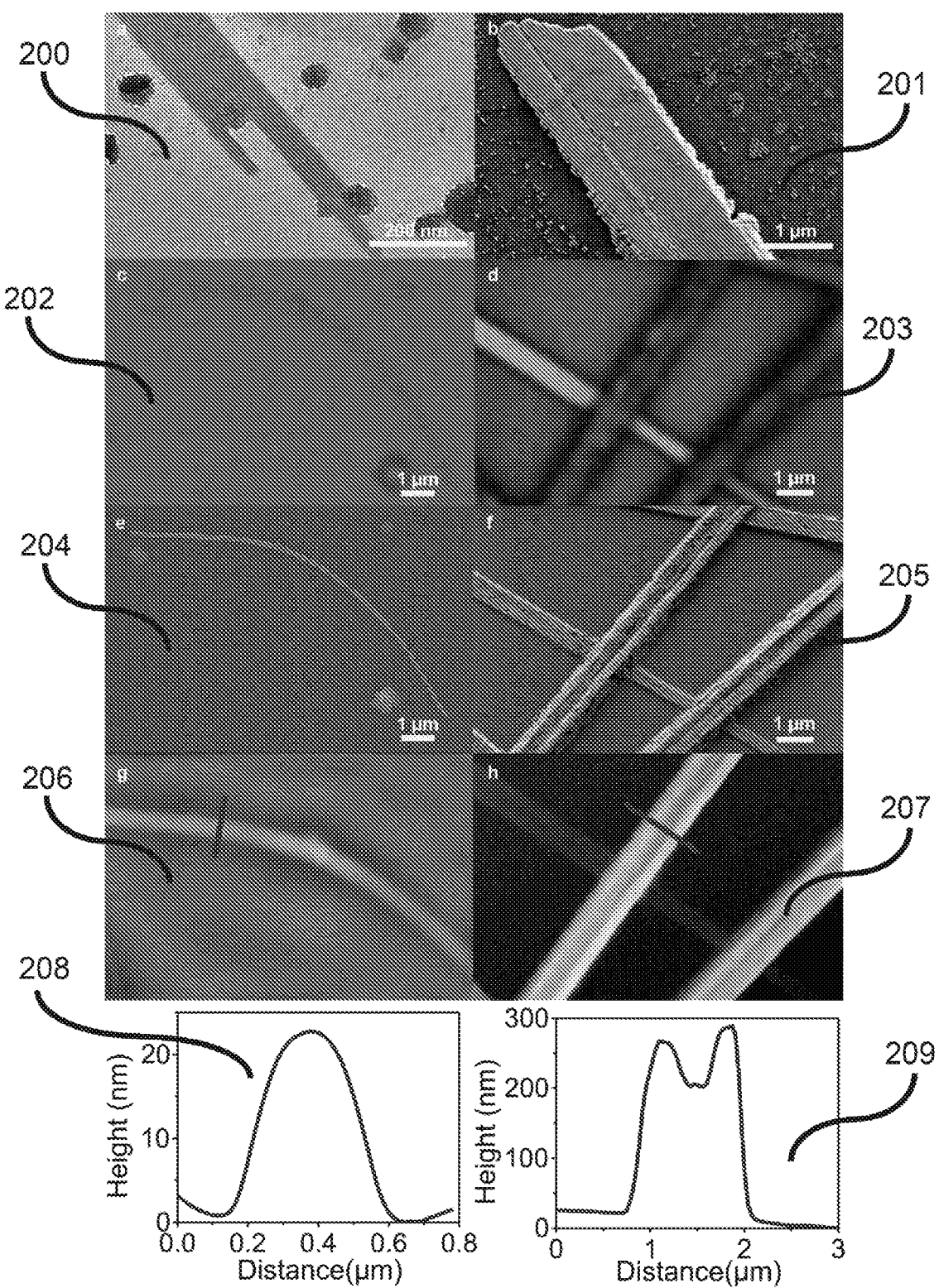
FIG. 2 contains views from a solid obtained with the steps of FIG. 1.

Optical microscopy was performed to confirm the crystallization of the solid. Unexpectedly, instead of a granular film composed of isotropic crystallites, a network of several micron long wire-like objects was observed, some of them pointing in the direction of sliding of the two glass plates (105,108). The filiform morphology was further confirmed using TEM (200), SEM (201, 205) and AFM (206-209) measurements as illustrated in FIG. 2.

Figure 3:
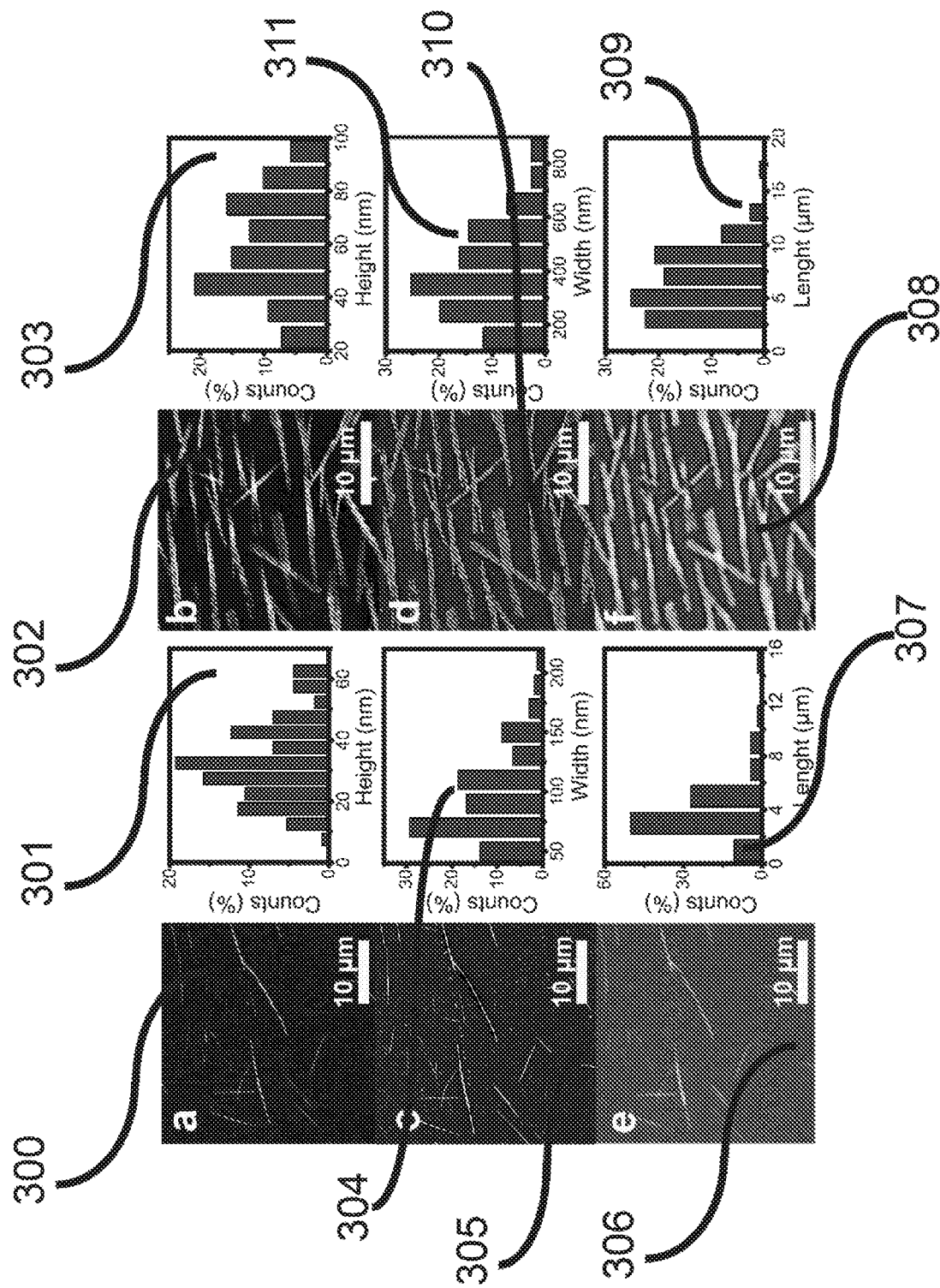
FIG. 3 contains views of nanowires.
Figure 7:
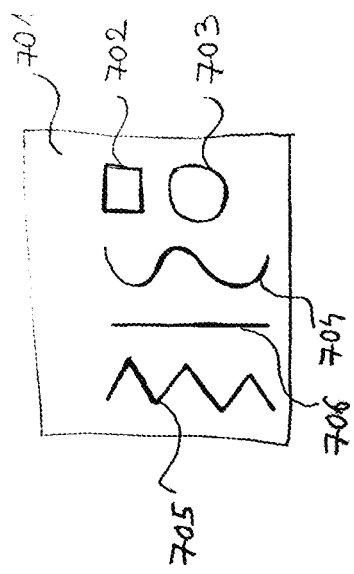
FIG. 7 illustrates different shapes of products obtained according to examples of the invention.
Figure 6:
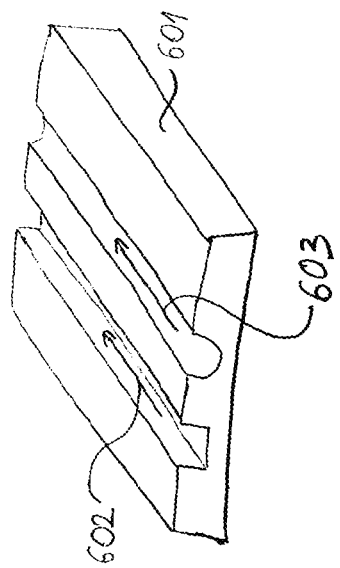
FIG. 6 illustrates a 3 dimensional view of a product obtained according to an example of the invention.

The width of the nanowires varied between 50 and 200 nm and they had lengths up to 16 microns. The height of the crystallites was determined from AFM measurements displaying a range from ultrathin (~9 nm) to several tens of nanometers thick (~90 nm) scale (300-311). The formation of a small number of aggregates of ~10 nm sized isotropic crystallites was also observed, as it can be seen on TEM and SEM micrographs (200, 202, 204, 206). These particles were homogeneously dispersed on the $SiO_2$ surface and attached to the wall of larger nanowires (201). Increasing the $MAPbI_3$ solution volume-to-surface ratio during the slip-coating process yields larger, sub-micron sized whiskers (201, 203, 205, 207). Unlike the thinner wires that have a flat surface, some of these thicker crystallites possess a U-shape void along their surface (207, 209). The size distribution of nanowires (read from optical, AFM and SEM images) prepared by two solution volumes is shown in FIG. 3 (300-311). We experienced that the parameters such as the solvent concentration, temperature, fluid philicity/phobicity, sliding speed etc. influence the kinetics of crystallization. We assume that the optimized combination of these parameters could result in a major product having well-controlled surface density, crystal habit, aspect ratio, size-distribution and even orientation on a given substrate (300-311, 601-603, 701-706) as illustrated in FIGS. 3, 6 and 7.

Figure 8:
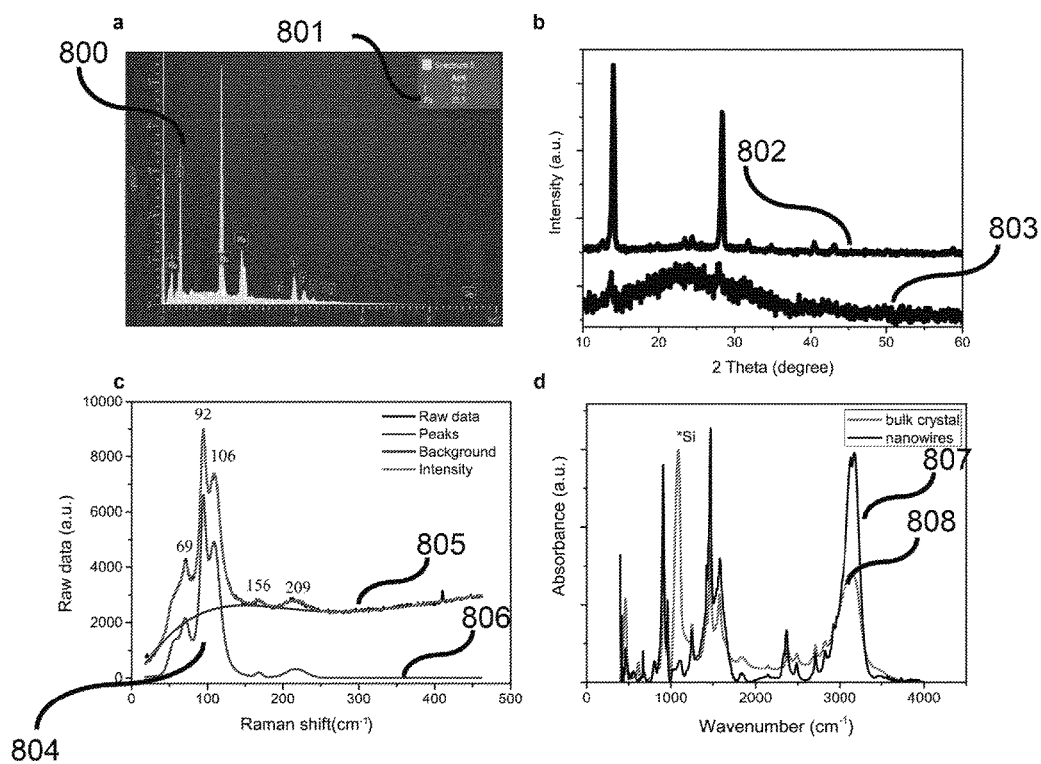
FIG. 8 contains measured spectra of materials comprised in nanowires according to examples of the invention.

Reference is now made to FIG. 8. The elemental composition of the anisotropic crystallites was analyzed by EDX. The presence of lead and iodine was readily confirmed, while the low atomic number carbon and nitrogen cannot be reliably quantified by EDX (800). The Pb:I atomic percent ratio was found to be 25:75 (800,801). To gain more insight into the structure of the nanowires XRD, Raman and infrared spectroscopies were performed. XRD diffractogram shows high intensity diffraction peaks at 2 Theta 14° (110) and 28.4° (220), which were identified as the characteristic peaks of the cubic $MAPbI_3$ phase[22] (802, 803). The presence of the low intensity peak at 12.54° is assigned to a $PbI_2$ phase which presumably formed as a result of the humidity-induced partial decomposition of $MAPbI_3$ during the PXRD measurement (802). The presence of two major reflection peaks suggests that the crystallites are highly oriented along the (110) direction. Raman spectra (804-806) recorded on filiform crystallites are also in accordance with the reported Raman modes of $MAPbI_3$[23]. Furthermore, Fourier Transform Infrared Spectroscopy (FTIR) spectra show a close correspondence in the vibration modes of filiform crystallites (807) and bulk single crystal (808) suggesting identical chemical composition ($CH_3NH_3PbI_3$).

The central question is where the directionality of the perovskite growth stems from. The role of the solvent in the nanowire formation was investigated by changing the solvent. The same protocol was repeated by replacing dimethyl formamide (DMF) by gamma-butyrolactone (GBL), another commonly used solvent of organolead halide perovskites. Due to the GBL's higher boiling point the evaporation was much slower, and ca. 350 K heat treatment was required to evaporate the solvent. Clearly, no anisotropic growth was taking place during the slip-coating process from GBL solution (900-902—FIG. 9). Thus, we assume that the use of DMF is the key step and therefore a unique role of DMF as a growth directing agent is suggested. It is not clear yet whether the DMF specifically affects the crystallization kinetics of the lead iodide framework or if the directional growth is due to an internal complex or adduct formation with the methylamine group. Currently we are assuming the second as a working hypothesis. The elucidation of the exact role of DMF on the formation of different solvatomorphs will be the subject of further studies.

The major interest in MAPbI$_3$ is its high sensitivity to visible-light, its high photovoltage of about 1.1 V which are the basic ingredients for an efficient solar-to-electric energy conversion[24]. These advantageous characteristics will certainly be explored in other device oriented research, like photodetection and solid state lasers[25]. The elucidation of the morphology dependent photoconductive performance could have a consequence on the development of more efficient devices. So far, the intrinsic photoconductive properties measured by standard contact method have not even been reported for the bulk samples. Here, we demonstrate the first results showing that one can make efficient photodetector based on nanowires of MAPbI$_3$. In addition, these findings are compared to the photodetection of a thin film of spin coated MAPbI$_3$ frequently used in photovoltaic devices.

Figure 4:
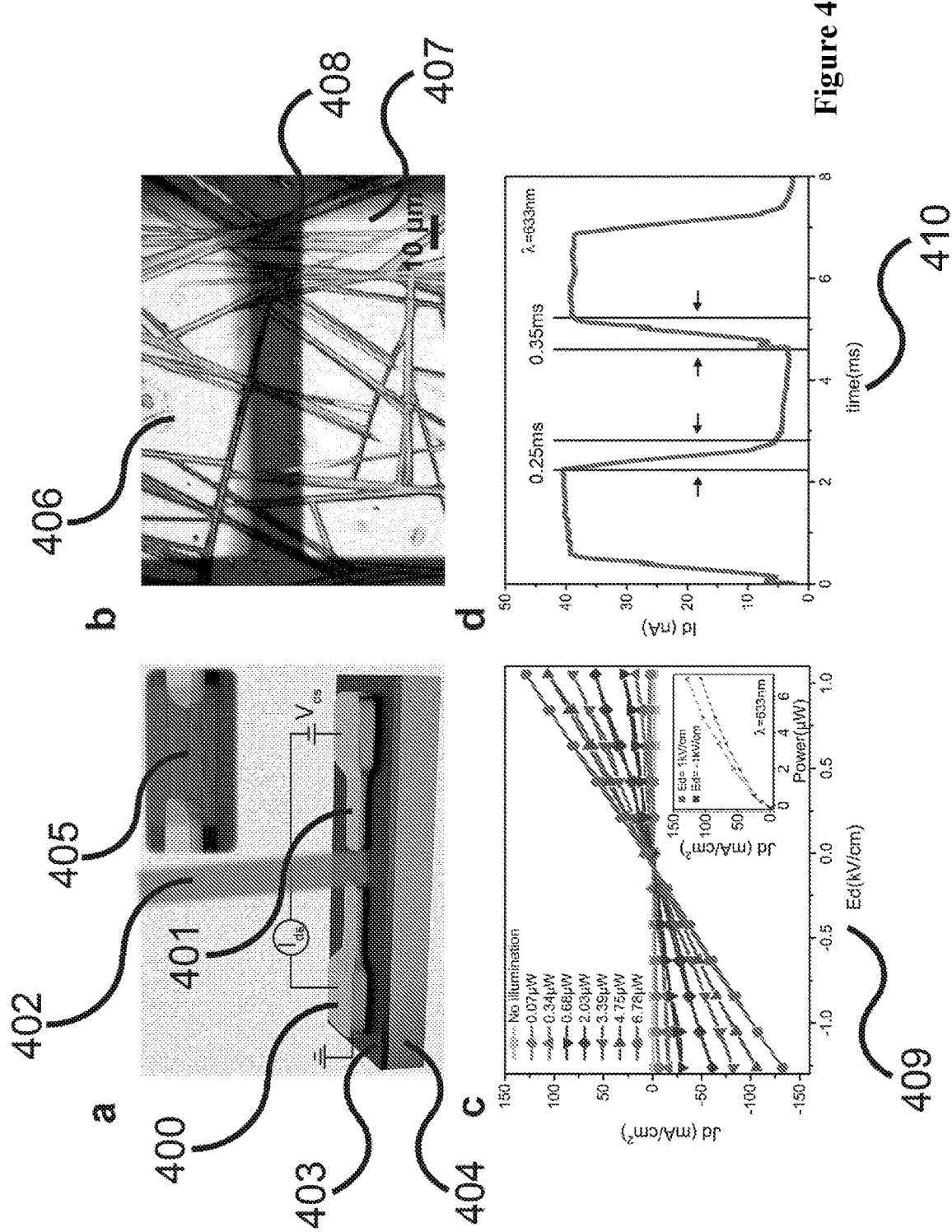
FIG. 4 shows a sketch and optical image of a device and nanowires according to the invention.

The devices were fabricated by slip-coating nanowires of different sizes of MAPbI$_3$ onto a highly p-doped silicon substrate with 300 nm SiO$_2$ on top. 100 nm-thick Pt contacts were deposited by e-beam evaporation through a microfabricated hard mask. The fabricated devices have a width of 100 μm and a length varying between 5 μm and 50 μm. The sketch of the device and the optical image of a real one are shown in FIG. 4 (400-408).

We measured the current density in the device as a function of the applied source-to-drain electric field in the dark and under illumination (red laser, λ=633 nm). The output characteristics follow a linear behavior, indicating that the contacts are ohmic (409). The contacts show a slight asymmetric behavior probably due to fabrication asymmetries.

In the dark state, the device behaves like a good insulator with currents of the order of tens of pA and resistances in the GOhm range. Under the illumination of the laser, the absorption of the light generates electron-hole pairs that are extracted by the source-to-drain electric field and cause an increase in the conductance of the material up to a factor of 300. We probed the photoresponse of the device under different incident laser powers in the 70 nW to 7 μW range. The current increases parabolically with the incident power, however, under the applied experimental conditions the saturation of the photocurrent has not been reached (409).

The device configuration allows to test the effect of a gate electric field on the I-V characteristics. Despite the semiconducting nature of the material, no influence of gating was noticed (1100-1103). The applicable electric field limit (break-down voltage) was determined to be ≈20 kV/cm. Higher electric fields risk an irreversible rupture of the filiform crystallites (1200-1203).

From the photocurrent one can estimate the responsivity of the device defined as $R=I_{ph}/P_{in}$, where $I_{ph}$ is the photocurrent and $P_{in}$ is the power of the incident light, respectively. For our device R was calculated to be 5 mA/W. Although, this value is about 4 orders of magnitude smaller than the best-in-class photoelectric devices made out of graphene and monolayer MoS$_2$[26,27,28,29], it is still comparable (10 times higher) to the value that has been achieved with the first prototypes of those 2D materials[30,31] (1400, 1500). Optimization of the device fabrication process and the engineering of its configuration might drastically improve the performances of the photodetectors based on filiform perovskites, similarly to how it happened for devices fabricated from graphene and MOS$_2$ (1400, 1500).

The response time of our device (410) showed that rise and decay times for the on-off current under illumination are less than 500 μs, ~10$^4$ faster than the state-of-the-art photodetectors made of monolayer MoS$_2$[26,28] and graphene[27,29,32]. The stability of the device was also tested by performing ~100 consecutive cycles measured over 1 h (1300). A slight increase of the photocurrent (~5%) is presumably due to contact adjustments (1300).

Figure 5:
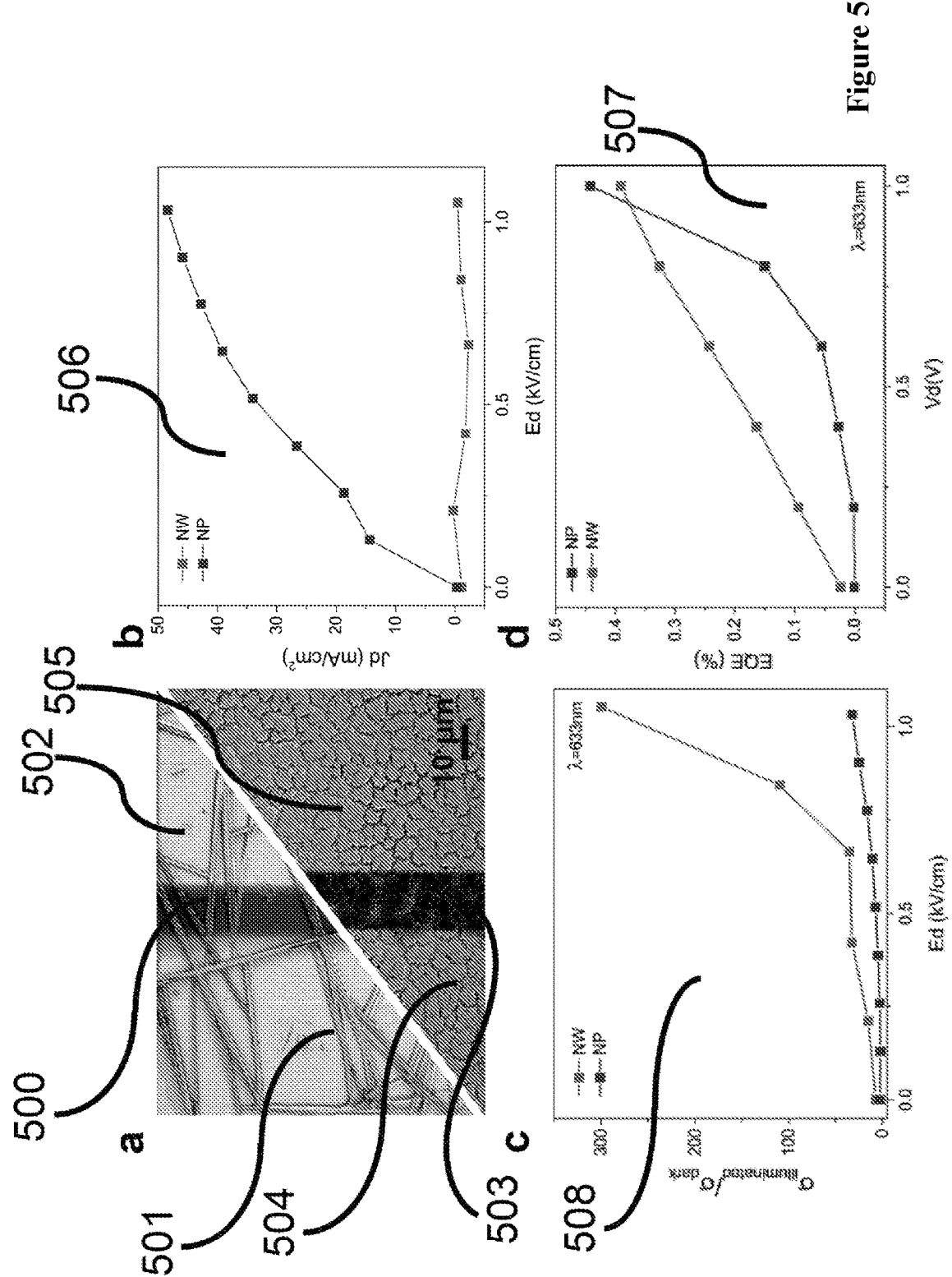
FIG. 5 contains graphs illustrating performances of a wire structure with respect to the spin coated film of prior art.

To compare the performance of the wire structure (500-502, 1001, 1004, 1005, 1008, 1009—FIGS. 5 and 10) with respect to the spin-coated film used today in solar cells, a photodetector with a film of MAPbI$_3$ nanoparticles was realized (503-505, 1000, 1002, 1003, 1006, 1007). Graph 506 in FIG. 5 gives the current density (calculated with the corresponding geometrical factors, details are in the Supplementary information) as a function of the source-drain voltage. The dark current measurements revealed that the reduced number of grain boundaries facilitates the flow of charge carriers, resulting in an increase in the current of ~160% for a source-to-drain voltage of IV (~1.1 kV/cm). The photocurrent-dark current ratio under a laser intensity of 2.5 Wcm$^{-2}$ (λ=633 nm) increases exponentially for the elongated perovskites while it is almost linear for the nanoparticles (508). The photocurrent-dark current ratio is one order of magnitude higher for filiform crystallites applying 1 kV/cm electric field. The performance limitations in the nanoparticle based film (most probably due to the increased number of grain boundaries) are also observable from the external quantum efficiency (EQE) defined as Rhv/e (details are in Supplementary information). For low voltages (<0.5V) the EQE of the device made of fibrous perovskites is twice as high as the photodetector prepared from MAPbI$_3$ nanoparticles.

These results demonstrate that the morphological properties, such as the crystallite size, form and their orientation could play an essential role in the photodetection and photoconductive response of the trihalide perovskite thin films.

Regarding the synthesis the Pb cation can be entirely or partially replaced by Sn, Ge, as well as transition metals cations as Mn, Fe, Co, Ni, Cu, Ag, Au etc. The organic cation can be entirely or partially replaced by other aliphatic amine molecules. The I anion can be entirely or partially replaced by F, Br or Cl anions. By applying these modifications the optoelectronic properties of the nanowires can be effectively tuned.

The nanowires crystallize on porous and/or solid insulator and/or conductive polymer, metal, ceramic surfaces. Surface structuring enables growth of linear, cylindrical motives with controlled morphology (see FIG. 6, 601-603, and FIG. 7, 701-706). In this case the nanowire growth is guided by the surface motifs non-soluble in polar aprotic solvents; the crystallization takes place inside the voids (602-603, 701-706).

The nanowires perpendicular to substrate can be grown by applying the perovskite DMF-DMSO solution on a porous functional surface containing parallel pores perpendicular to the surface.

The relevant example, that recrystallization from solvents of different nature facilitates forming of elongated solvatomorphs of organic-inorganic perovskite (e.g. lead-methylamine iodide) is a new solution-mediated strategy with which we exerting control over crystallite characteristics. The optically active elongated form of trihalide perovskites will make it possible to explore exiting opportunities in photonics industry such as solar energy conversion, photodetectors and on-chip coherent light sources.

Details of the Sample Preparation and Characterization of the Devices

Synthesis of MAPbI3 Nanocrystallites by Slip-Coating Method (100-108)

MAPbI$_3$ single crystals and polycrystalline powder was synthesized using the method described by Poglitch and Weber.[33] The as-prepared polycrystalline powder was dissolved in organic solvents.

Filiform crystallites: 10 microliters of saturated solution (≈50 w %) of MAPbI$_3$ in dimethyl formamide (DMF, Sigma-Aldrich) was dropped onto a microscope glass slide (Thermoscientifictype, 76×26 mm) and covered with a second microscope slide so that the yellow solution spreads out and forms a homogenous liquid film between the glass plates (FIG. 1, 100-106). From the borders the excess of the MAPbI$_3$ solution was removed by soaking with a tissue. Next, the bottom substrate was fixed and we started gradually to slide the upper glass slide while exposing the thin liquid film to air (106). Solvent evaporation from the uncovered surface caused an instantaneous yellow to brown-red color change (107). Unless otherwise specified, the same protocol was applied on SiO$_2$ covered microfabricated chips.

Nanoparticle based films: were prepared by identical procedure described above applying saturated solution (40 w %) of MAPbI$_3$ in gamma-Butyrolactone (GBL, Sigma-Alrich) solvent (FIG. 9, 900-902).

Material Characterization

Energy Dispersive X-ray Spectroscopy (EDX)

Scanning Electron Microscope images were taken with a MERLIN Zeiss electron microscope. The elemental composition of the fibrous crystallites was analyzed by EDX (accelerating voltage of 8 kV, working distance of 8.5 cm).

FIG. 8 (800-801) shows EDX spectra of MAPbI$_3$ nanowires. Pb:I ratio is close to the stoichiometric value of 1:3.

Powder X-Ray Diffraction (XRD)

X-ray diffraction patterns were collected on a RIGAKU using a source of Cu Kλ (1.54050 Å). XRD results suggest that highly oriented MAPbI$_3$ crystallites (along the (110) direction) are present on the substrate. In Fig (802-803) the low intensity wide diffraction peak centered at 2 Theta 24 degree comes from the microscope glass slides support.

FIG. 8, references 803-804 show PXRD diffractogram of the as prepared MAPbI$_3$ nanowires (803, 804).

Raman Spectroscopy

The structure of the filiform perovskites was analyzed by Raman spectroscopy (HORIBA LabRAM HR Raman spectrometer). Spectra were taken using an 532 nm green excitation laser. Laser power was reduced in order to avoid photodegradation of the sample. Focalspot size was about 10 µm using a 50× long working distance objective. The recorded Raman spectrum shows great similarities with the reported Raman modes of MAPbI$_3$.

FIG. 8, references 804-806: Raman spectrum of MAPbI$_3$ nanowires slip-coated on SiO$_2$/Si substrate. Numbers indicate the frequency of the measured lines.

Fourier Transform Infrared Spectroscopy (FTIR)

Measurements were performed with a Bruker Tensor FTIR spectrometer with a DTGS detector and 4 wavenumber resolution. The bulk crystal was measured in transmission mode on Si while the diffuse reflectance (DRIFT) mode was employed for the analysis of the nanowires. For the DRIFT we used an integration sphere and a flat gold surface as a reference. The vibration modes in the FT-IR spectrum of filiform crystallites shows great similarities to those obtained on bulk single crystal suggesting identical chemical composition (CH$_3$NH$_3$PbI$_3$).

FIG. 8, references 807-808: FTIR spectra obtained for MAPbI$_3$ nanowires and a bulk crystal of CH$_3$NH$_3$PbI$_3$. The Si—O vibration of the substrate is marked with an asterisk.

Slip-Coating with GBL

Figure 9:
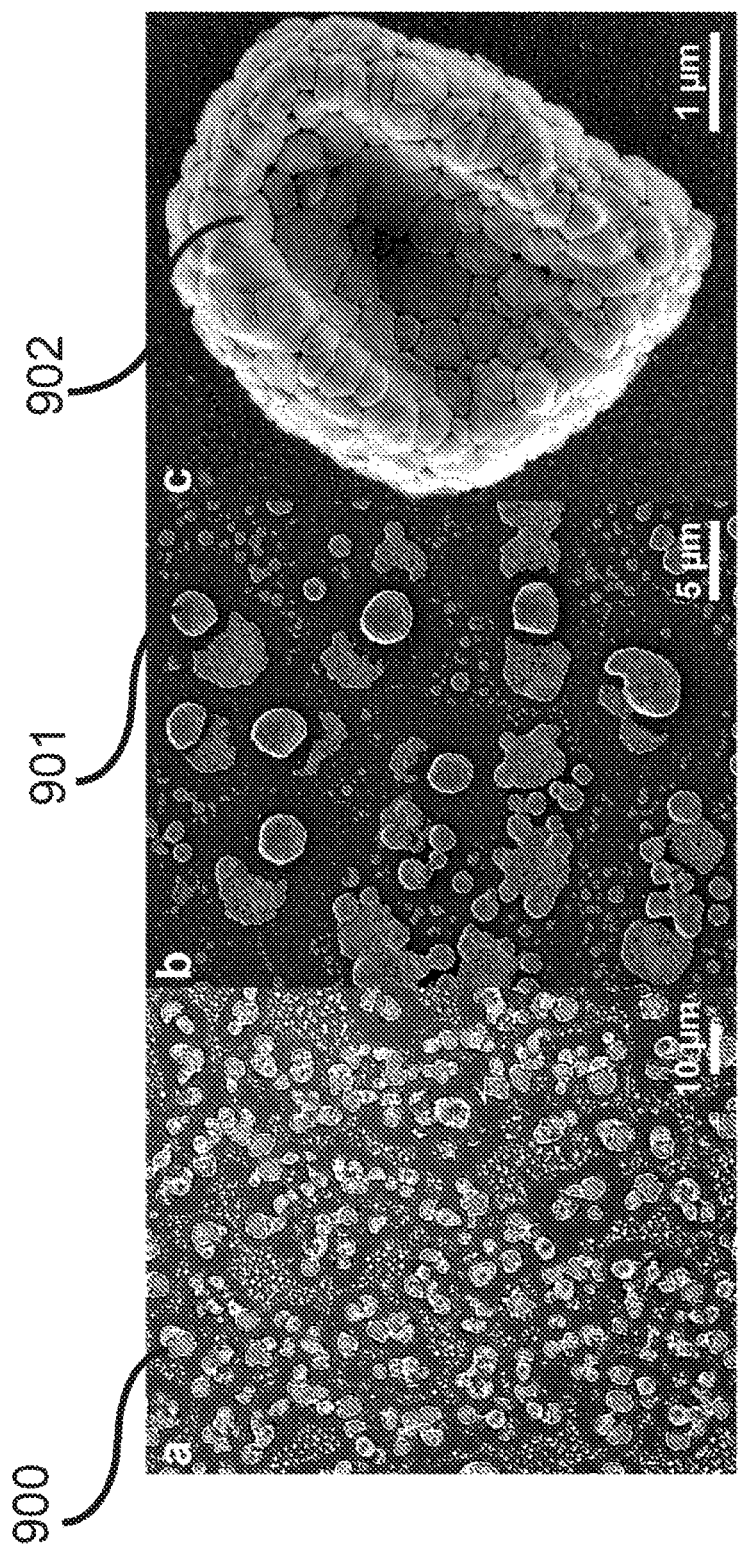
FIG. 9 contains pictures representative of anisotropic growth.

FIG. 9, references 900-902: Optical (900) and SEM (901,902) analysis of slip-coated MAPbI$_3$ with GBL solvent. All images show the absence of filiform crystallites and the formation of particle agglomerates (902).

Device Fabrication

The devices were fabricated by slip-coating of MAPbI$_3$ solution (GBL-nanoparticles, DMF-filiform crystallites) onto a highly p-doped silicon substrate with 300 nm thermally grown SiO$_2$ on top. Source and drain contacts were patterned by an e-beam evaporation (Leybold Optics LAB 600 H) of 100 nm of Pt in high vacuum (<10$^{-6}$ mbar, room temperature) through a microfabricated hard mask. The fabricated contact pads had a width of 100 µm and a length varying between 5 µm and 50 µm. The sketch and an optical microscopy image of a representative device are shown in FIG. 4, reference 400-405 and 406-408.

Device Characterization

Electrical Measurements

If it is not otherwise specified all measurements were performed on freshly prepared samples under ambient conditions. Two-point electrical measurements (d.c.) were carried out using a National Instruments GPIB-USB-HS controller and a Keithely 2400 source meter. To minimize sources of external noise, the measurements were performed in a home-built Faraday cage. A microscope objective and a micromechanical stage were used to localize the device.

Photocurrent Measurements

We probed the devices and their time-dependent responsivity to laser excitation using a laser beam (COHERENT laser module, model 31-1050, λ=633 nm) with an illumination power from 0.1 mW to 10 mW. The spot size had a diameter of 4 mm, resulting in an estimated maximum illumination power of 0.25 Wcm$^{-2}$. The time response of the photocurrent was acquired by modulating the laser beam with a mechanical chopper (217 Hz) and detecting the photocurrent with a current preamplifier (FIG. 10: 1100-1102).

Device Geometry Calculations

Figure 10:
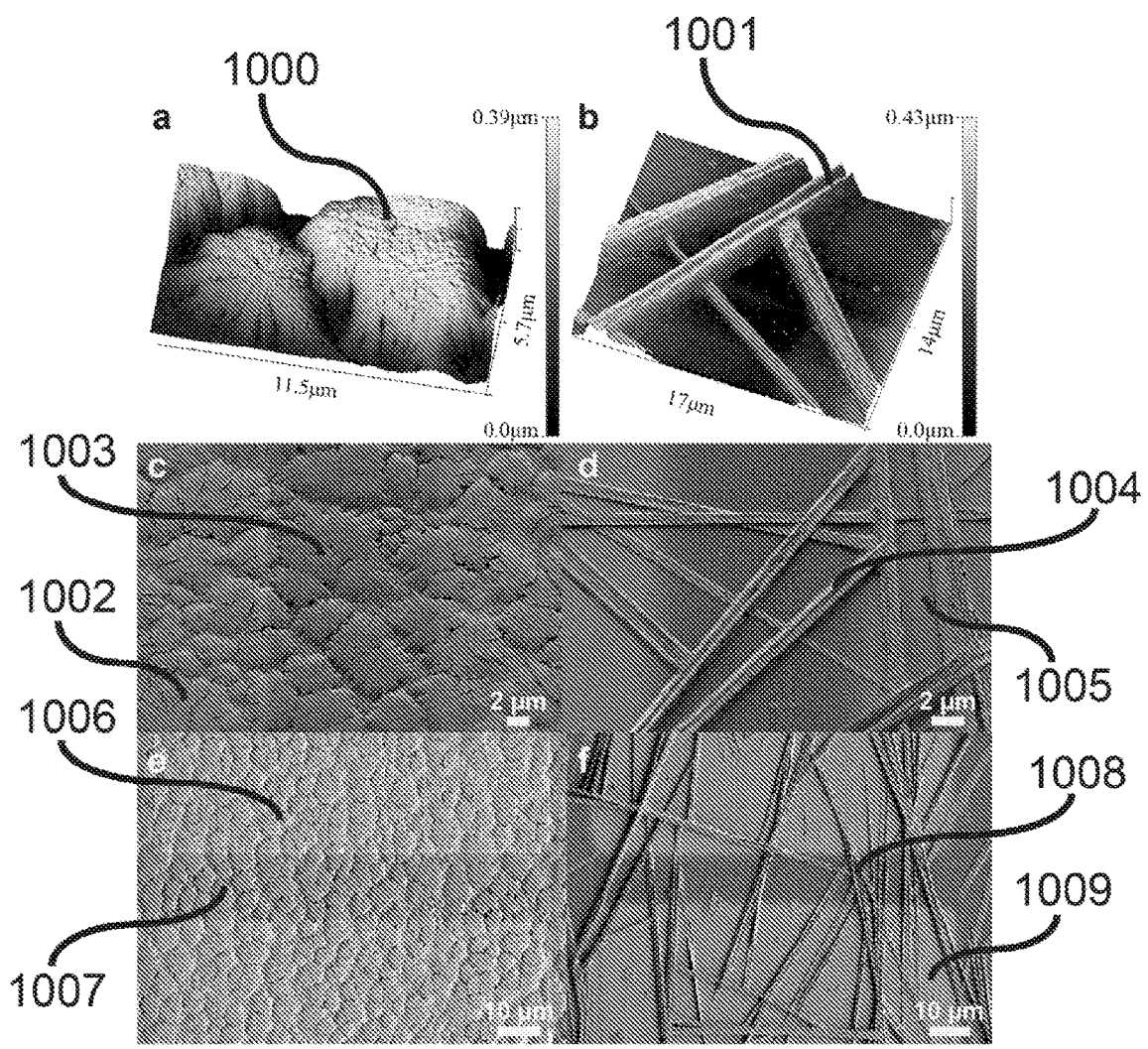
FIG. 10 contains picture and measurements of nanowires.

The geometrical factors used for the performance calculations of the photodetectors were extracted from the AFM and SEM analysis of the fabricated devices (FIG. 10: 1000-1009). The height of the MAPbI$_3$ nanowires and nanoparticles was measured with a Bruker Dimension FastScan atomic force microscope (in tapping mode, 1000, 1001). The width and length of the nanostructured MAPbI$_3$ was determined from SEM (Scanning Electron Microscope) images (MERLIN Zeiss SEM operating at 1 kV and a working distance of ~4 mm, 1002-1009). The active area of the devices made of filiform perovskites contained several crystallites (FIG. 10: 1008-1009). In this case the calculations were done by summing up the dimensions of individual nanowires lying in the active area (1001, 1004-1005).

For the nanoparticles, a mean value of their height was used and a uniform coverage of the contacts was assumed (1000, 1006-1007).

FIG. 10: references 1000-1009: AFM (1000, 1001) and SEM (1002, 1009) of several MAPbI$_3$ nanoparticles (1000, 1002-1003, 1006-1007) and nanowires (1001, 1004-1005, 1008-1009) used in the fabrication of photodetectors made with nanostructured perovskites.

Effect of the Gate Voltage

Figure 11:
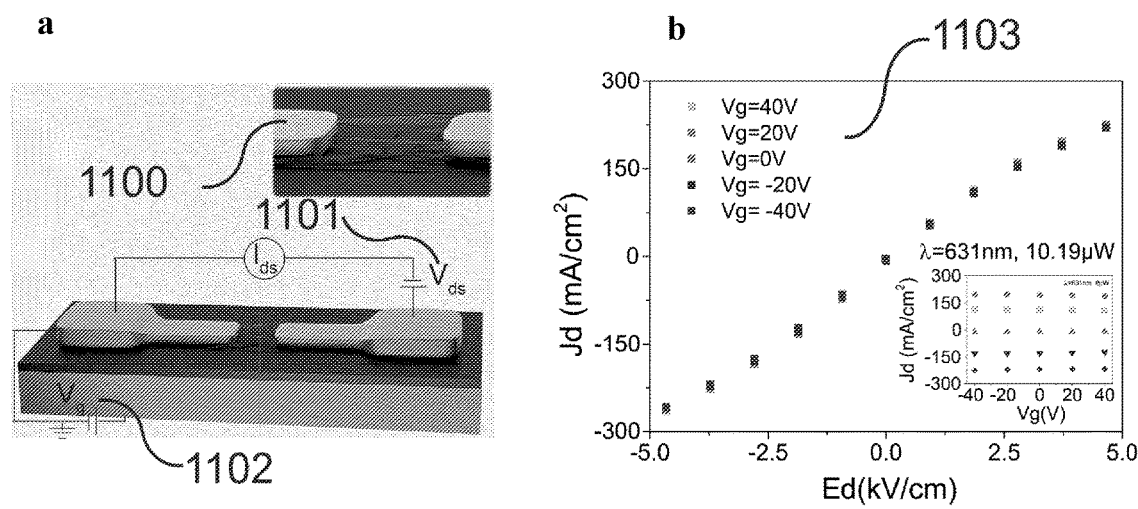
FIG. 11 contains an example of a photodetector made of filiform perovskites.

We tested the effect of a transversal electric field applied on the semiconducting MAPbI$_3$ nanowire channel. The device configuration is shown in FIG. 11, references 1100-1102. A constant gate voltage (up to ±40 V) was applied while sweeping the source-to-drain electric field between −5 k V/cm and +5 k V/cm. Surprisingly, even for realatively high gate voltages (±40 V) no modulation of the charge carrier concentration was observed (1103).

FIG. 11, references 1100-1103: schematic representation of the photodetector made of filiform perovskites (1100-1102) output characteristics of the tested device (1103) for different gate voltages. As we can clearly see from the inset, the gate voltage has no influence on the measured current density.

Breakdown Voltage of the Photodetector Made with Filiform Perovskites

Figure 12:
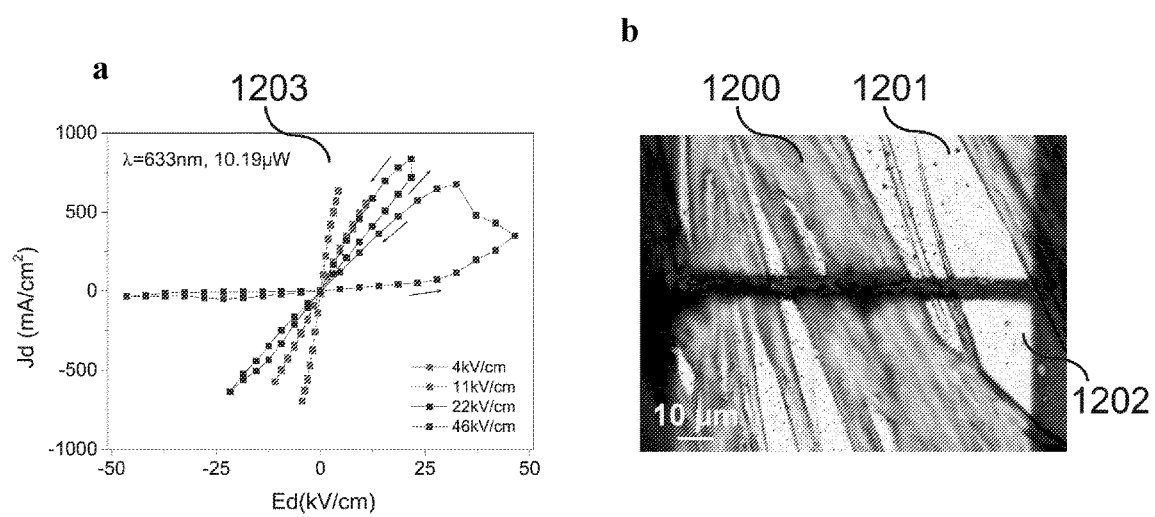
FIG. 12 contains an output characteristic of a device made of $MAPbI_3$ nanowires with increasing longitudinal field.

To study the performance limit and the maximum electric field applicable to the MAPbI$_3$ nanowires under illumination we tested several devices under increasing source-to-drain electric field (an example is shown in 1200-1203). FIG. 12, reference 1203 shows that when applying a longitudinal field larger than 20 kV/cm the repeated I-V curves start to diverge. Decreasing photocurrent and an increasing hysteresis loop appears in the output characteristic (1203, curve 3). Electric field to values larger than 30 kV/cm causes the total breakdown of the device (1200-1202).

FIG. 12, references 1200-1203: output characteristic of a device made of MAPbI$_3$ nanowires with increasing longitudinal field (a). An electric field bigger than 30±10 kV/cm causes the irreversible rupture of the microwires (b).

Stability of the Photodetector Based on MAPbI$_3$ Nanowires

Figure 13:
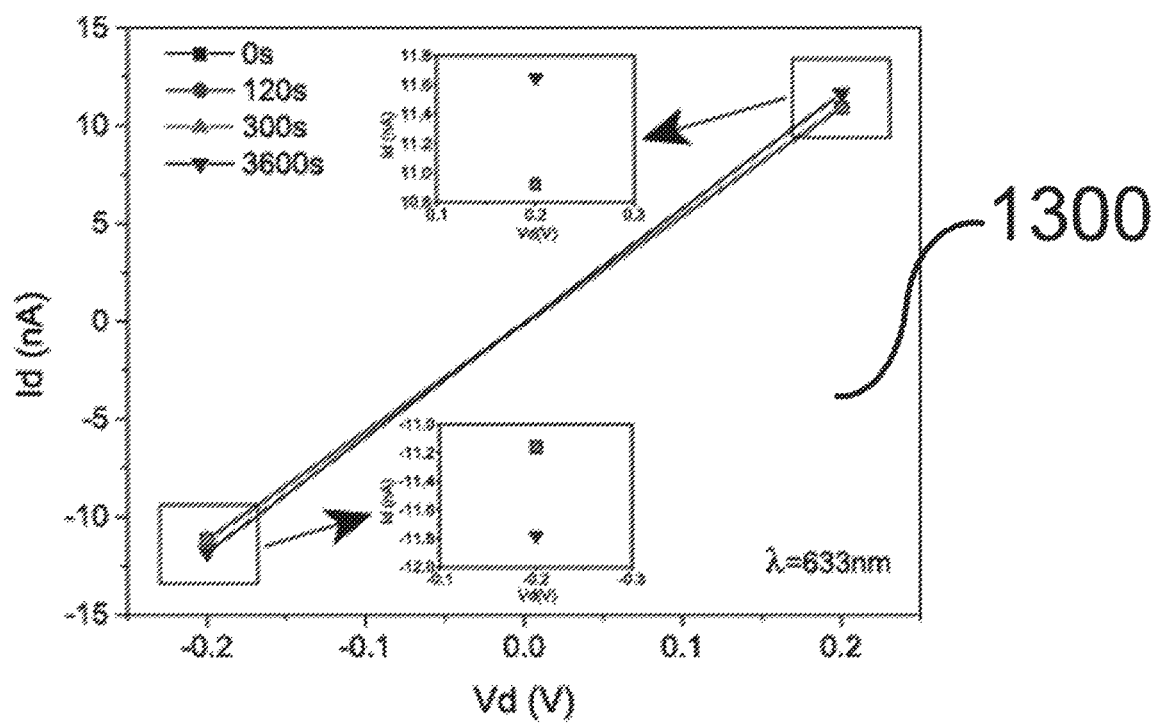
FIG. 13 shows a photocurrent of a $MAPbI_3$ nanowires device after several consecutive cycles.

Referring to FIG. 13, we tested the reliability of the fabricated photodetector by measuring the photocurrent of the device for ~100 cycles (from −200 mV to +200 mV) and a measurement time of ~1 h. In order to prevent humidity induced degradation of the material a drop-casted top PMMA layer (A4) was applied prior the device cyclability test. The device showed identical I-V characteristics up to <300 s. After 1 h of continuous measurement, the photocurrent increased of ~5%—this improvement is presumably due to some contacts adjustments.

FIG. 13, reference 1300: photocurrent of the device after several consecutive cycles. The current is stable until (300 s) and it is increasing with time of about 5% (probably because of contacts adjustment).

External Quantum Efficiency Calculation

The external quantum efficiency (E.Q.E.) is the ratio of the number of carriers generated and collected by the photodetector to the number of photons of a given energy incident on the device. For a given incident optical power P$_{in}$ and a generated photocurrent I$_{ph}$, it can be calculated by:

$$\frac{I_{ph}/e}{P_{in}/hv} \qquad \text{(equation 1)}$$

where e is elementary charge, h is the Planck constant and v is the speed of light.

The performances of the devices based on nano-perovskites were calculated by assuming that all the incident light was absorbed by the device and converted into electron-hole pairs, thus neglecting the effect of optical losses such as transmission and reflection. It is important to mention, that the transmission and reflection losses have not been determined in this work. Since the presence of these optical phenomena could highly affects the calculated EQE, in our case the reported values can be seen as characteristic lower bound values for this material.

Responsivity of State-Of-The-Art Photodetectors

Figure 14:
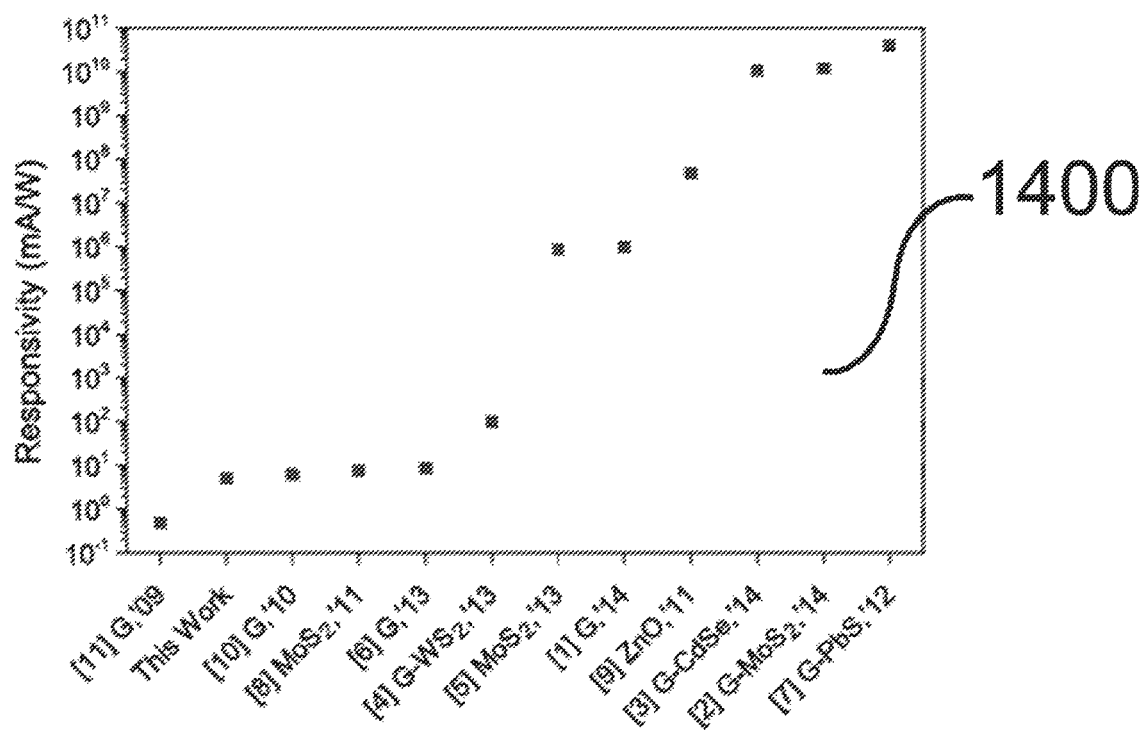
FIG. 14 illustrates photoresponsivity of several recent state-of-the-art photodetectors based on nanomaterials.

FIG. 14, reference 1400: photoresponsivity of several recent state-of-the-art photodetectors based on nanomaterials.

FIG. 15, reference 1500: compilation of several recent photodetectors made of nanomaterials.

CONCLUSION

The invention relates to one-dimensional elongated organic-inorganic perovskites crystallites, in particular hyper-branched and/or aligned nano—and microwires parallel or perpendicular to the substrate. The nano—and microwires can be made by solution mixing, slip-coating, spin coating, doctor blading or spraying of solution of pure solvents or solvent mixtures of polar aprotic solvents e.g. dimethyl formamide (DMF), dimethyl sulfoxide (DMSO), dimethylacethamide (DMAc) containing Pb cations, methylamine and I anions in 1:1:3 stoichiometric ratio. The Pb cation can be entirely or partially replaced by Sn, Ge, as well as transition metals cations as Mn, Fe, Co, Ni, Cu, Ag, Au etc. The organic cation can be entirely or partially replaced by other aliphatic amine molecules or alkali cations as Na, K, Li, Cs, Rb. The I anion can be entirely or partially replaced by F, Br or Cl anions. The temperature range for anisotropic crystallization falls between 273-373 K. The time-scale of the fabrication process is between 5 and 1200 seconds. The nanowires obtained by this method have length-width aspect ratio from 5-400 and width-height ratio of 1-100. The nanowires crystallize on porous and/or solid insulator and/or conductive polymer, metal, ceramic surfaces. Surface structuring enables growth of linear, cylindrical motives with controlled morphology. The organic-inorganic nanowires can be used as Gamma-Ray, X-Ray, UV, Vis and NIR detector. It can be used in mesoscopic solar cells, LED, OLED and in systems where light amplification by stimulated emission of radiation is used. The one dimensional form of MAPbI$_3$ could have unique optical and electrical properties. The feasibility of anisotropic growth of organolead halide perovskites opens up a new strategy towards the realization of low-temperature, solution processed films with controlled morphology.

REFERENCES

1 Zhang, A., Cheng, J., Kim, H., Liu, Y. S. & Lo, Y. H. Characterization and physics of top-down silicon nanowire phototransistors. *Quantum Sensing and Nanophotonic Devices Vii* 7608, doi:Artn 76081d, Doi 10.1117/12.841201 (2010).
2 Kojima, A., Teshima, K., Shirai, Y. & Miyasaka, T. Organometal Halide Perovskites as Visible-Light Sensitizers for Photovoltaic Cells. *J Am Chem Soc* 131, 6050-6051, doi:10.1021/ja809598r (2009).
3. Liu, C.-H., Chang, Y.-C., Norris, T. B. & Zhong, Z. Graphene photodetectors with ultra-broadband and high responsivity at room temperature. *Nat Nano* advance online publication, doi:10.1038/nnano.2014.31, http://www.nature.com/nnano/journal/vaop/ncurrent/abs/nnano.2014.31.html#supplementary-information (2014).
4. Mosconi, E., Amat, A., Nazeeruddin, M. K., Grätzel, M. & De Angelis, F. First-Principles Modeling of Mixed Halide Organometal Perovskites for Photovoltaic Applications. *The Journal of Physical Chemistry C* 117, 13902-13913, doi:10.1021/jp4048659 (2013).
5. Kim, H.-S. et al. Lead Iodide Perovskite Sensitized All-Solid-State Submicron Thin Film Mesoscopic Solar Cell with Efficiency Exceeding 9%. *Sci. Rep.* 2, doi:http://www.nature.com/srep/2012/120821/srep00591/abs/srep00591.html#supplementary-information (2012).
6. Docampo, P., Ball, J. M., Darwich, M., Eperon, G. E. & Snaith, H. J. Efficient organometal trihalide perovskite planar-heterojunction solar cells on flexible polymer substrates. *Nat Commun* 4, doi:10.1038/ncomms3761 (2013).
7. Xing, G. et al. Long-Range Balanced Electron- and Hole-Transport Lengths in Organic-Inorganic CH3NH3PbI3. *Science* 342, 344-347, doi:10.1126/science.1243167 (2013).
8. Im, J.-H., Lee, C.-R., Lee, J.-W., Park, S.-W. & Park, N.-G. 6.5% efficient perovskite quantum-dot-sensitized solar cell. *Nanoscale* 3, 4088-4093, doi:10.1039/C1NR10867K (2011).
9. Stranks, S. D. et al. Electron-Hole Diffusion Lengths Exceeding 1 Micrometer in an Organometal Trihalide Perovskite Absorber. *Science* 342, 341-344, doi:10.1126/science.1243982 (2013).
10. Colella, S. et al. MAPbI3-xClx Mixed Halide Perovskite for Hybrid Solar Cells: The Role of Chloride as Dopant on the Transport and Structural Properties. *Chem Mater* 25, 4613-4618, doi:10.1021/cm402919x (2013).
11. Edri, E. et al. Why Lead Methylammonium Tri-Iodide Perovskite-Based Solar Cells Require a Mesoporous Electron Transporting Scaffold (but Not Necessarily a Hole Conductor). *Nano Lett* 14, 1000-1004, doi:10.1021/nl404454h (2014).
12. Pang, S. et al. NH2CH=NH2PbI3: An Alternative Organolead Iodide Perovskite Sensitizer for Mesoscopic Solar Cells. *Chem Mater* 26, 1485-1491, doi:10.1021/cm404006p (2014).
13. Noh, J. H., Im, S. H., Heo, J. H., Mandal, T. N. & Seok, S. I. Chemical Management for Colorful, Efficient, and Stable Inorganic-Organic Hybrid Nanostructured Solar Cells. *Nano Lett* 13, 1764-1769, doi:10.1021/nl400349b (2013).
14. Kulkarni, S. A. et al. Band gap tuning of lead halide perovskites using a sequential deposition process. *J Mater Chem A*, doi:10.1039/C4TA00435C (2014).
15. Im, J.-H., Chung, J., Kim, S.-J. & Park, N.-G. Synthesis, structure, and photovoltaic property of a nanocrystalline 2H perovskite-type novel sensitizer (CH3CH2NH3)PbI3. *Nanoscale Res Lett* 7, 353 (2012).
16. Ball, J. M., Lee, M. M., Hey, A. & Snaith, H. J. Low-temperature processed meso-superstructured to thin-film perovskite solar cells. *Energy & Environmental Science* 6, 1739-1743, doi:10.1039/C3EE40810H (2013).
17. Burschka, J. et al. Sequential deposition as a route to high-performance perovskite-sensitized solar cells. *Nature* 499, 316-319, doi:10.1038/nature12340, http://www.nature.com/nature/journal/v499/n7458/abs/nature12340.html#supplementary-information (2013).
18. Wojciechowski, K., Saliba, M., Leijtens, T., Abate, A. & Snaith, H. J. Sub-150 [degree] C. processed meso-super-structured perovskite solar cells with enhanced efficiency. *Energy & Environmental Science* 7, 1142-1147, doi:10.1039/C3EE43707H (2014).
19. Eperon, G. E., Burlakov, V. M., Docampo, P., Goriely, A. & Snaith, H. J. Morphological Control for High Performance, Solution-Processed Planar Heterojunction Perovskite Solar Cells. *Advanced Functional Materials* 24, 151-157, doi:10.1002/adfm.201302090 (2014).
20. Liu, M., Johnston, M. B. & Snaith, H. J. Efficient planar heterojunction perovskite solar cells by vapour deposition. *Nature* 501, 395-398, doi:10.1038/nature12509 (2013).
21. Qin, P. et al. Yttrium-substituted nanocrystalline TiO2 photoanodes for perovskite based heterojunction solar cells. *Nanoscale* 6, 1508-1514, doi:10.1039/C3NR05884K (2014).
22. Baikie, T. et al. Synthesis and crystal chemistry of the hybrid perovskite (CH3NH3)PbI3 for solid-state sensitised solar cell applications. *J Mater Chem A* 1, 5628-5641, doi:10.1039/C3TA10518K (2013).
23. Quarti, C. et al. The Raman Spectrum of the CH3NH3PbI3 Hybrid Perovskite: Interplay of Theory and Experiment. *The Journal of Physical Chemistry Letters* 5, 279-284, doi:10.1021/jz402589q (2013).
24. Lee, M. M., Teuscher, J., Miyasaka, T., Murakami, T. N. & Snaith, H. J. Efficient Hybrid Solar Cells Based on Meso-Superstructured Organometal Halide Perovskites. *Science* 338, 643-647, doi:10.1126/science.1228604 (2012).
25. Xing, G. et al. Low-temperature solution-processed wavelength-tunable perovskites for lasing. *Nat Mater* advance online publication, doi:10.1038/nmat3911, http://www.nature.com/nmat/journal/vaop/ncurrent/abs/nmat3911.html#supplementary-information (2014).
26. Zhang, W. J. et al. Ultrahigh-Gain Photodetectors Based on Atomically Thin Graphene-MoS2 Heterostructures. *Sci Rep-Uk* 4, doi:Artn 3826, Doi 10.1038/Srep03826 (2014).
27. Jin, W. et al. Novel graphene-oxide-semiconductor nanowire phototransistors. *Journal of Materials Chemistry C* 2, 1592-1596, doi:10.1039/C3TC32123A (2014).
28. Lopez-Sanchez, O., Lembke, D., Kayci, M., Radenovic, A. & Kis, A. Ultrasensitive photodetectors based on monolayer MoS2. *Nat Nano* 8, 497-501, doi:10.1038/nnano.2013.100, http://www.nature.com/nnano/journal/v8/n7/abs/nnano.2013.100.html#supplementary-information (2013).
29. Konstantatos, G. et al. Hybrid graphene-quantum dot phototransistors with ultrahigh gain. *Nat Nano* 7, 363-368, doi:http://www.nature.com/nnano/journal/v7/n6/abs/nnano.2012.60.html#supplementary-information (2012).
30. Xia, F. N., Mueller, T., Lin, Y. M., Valdes-Garcia, A. & Avouris, P. Ultrafast graphene photodetector. *Nat Nanotechnol* 4, 839-843, doi:Doi 10.1038/Nnano.2009.292 (2009).
31. Yin, Z. Y. et al. Single-Layer MoS2 Phototransistors. *Acs Nano* 6, 74-80, doi:Doi 10.1021/Nn2024557 (2012).
32. Zhang, Y. Z. et al. Broadband high photoresponse from pure monolayer graphene photodetector. *Nature Communications* 4, doi:Artn 1811, Doi 10.1038/Ncomms2830 (2013).
33. Poglitsch, A. & Weber, D. Dynamic disorder in methyl-ammoniumtrihalogenoplumbates (II) observed by millimeter☐ wave spectroscopy. *The Journal of Chemical Physics* 87, 6373-6378, doi:doi:http://dx.doi.org/10.1063/1.453467 (1987).

The invention claimed is:

1. A halide perovskite nanowire comprising:
a halide perovskite body having dimensions of length, wide, and height;
wherein the halide perovskite body has a length-width aspect ratio between 5-400 and 5-$10^9$ and a width-height ratio between 1-100 and 1-10000.

2. The nanowire according to claim 1, wherein the halide perovskite body is composed of methylammonium lead iodide ($CH_3NH_3PbI_3$).

3. The nanowire according to claim 1, wherein the halide perovskite body is composed of $ABX_3$ where A is an aliphatic amine and/or alkali cation, B is a transition metal and/or a noble metal, and X is a Cl, Br or I anion.

4. A mesoscopic or planar heterojunction single or tandem solar cell made of nanowires as defined in claim 1.

5. A gamma-ray, or X-ray, or visible light, or near infrared detector made of nanowires as defined in claim 1.

6. A light amplification by stimulated emission of radiation system made of nanowires as defined in claim 1.

7. A LED or OLED made of nanowires as defined in claim 1.

8. A magneto-optical data storage element made of nanowires as defined in claim 1.

* * * * *

UNITED STATES PATENT AND TRADEMARK OFFICE
CERTIFICATE OF CORRECTION

PATENT NO. : 10,529,498 B2  
APPLICATION NO. : 15/313153  
DATED : January 7, 2020  
INVENTOR(S) : Horváth et al.

Page 1 of 1

It is certified that error appears in the above-identified patent and that said Letters Patent is hereby corrected as shown below:

On the Title Page

The assignee city name is spelled incorrectly in item "(73)". Instead of "Luasanne", the assignee city name should be: "Lausanne"

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*